United States Patent
Chun et al.

(10) Patent No.: US 6,463,790 B1
(45) Date of Patent: Oct. 15, 2002

(54) MEMBRANE FILTRATION METHOD AND APPARATUS FOR SIMULTANEOUSLY AND CONTINUOUSLY MONITORING TIME-BASED MEMBRANE FOULING

(75) Inventors: Myung-Suk Chun; Jae-Jin Kim; Sang-Yup Lee, all of Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 44 days.

(21) Appl. No.: 09/678,829

(22) Filed: Oct. 4, 2000

(30) Foreign Application Priority Data

May 24, 2000 (KR) .............................. 00-27910

(51) Int. Cl.⁷ ..................... G01N 11/04; G01N 15/08; G01N 15/02
(52) U.S. Cl. .................... 73/38; 73/64.56; 73/61.73; 210/741; 210/746
(58) Field of Search ............... 73/38, 64.56, 61.73, 73/53.04, 61.47; 210/500.22, 741, 746

(56) References Cited

U.S. PATENT DOCUMENTS

| | | | |
|---|---|---|---|
| 3,590,634 A | * 7/1971 | Pasternak | 73/159 |
| 3,718,434 A | * 2/1973 | Pierce | 23/232 R |
| 3,824,823 A | * 7/1974 | Pontello | 73/432 |
| 3,926,561 A | * 12/1975 | Lucero | 23/232 R |
| 3,939,457 A | * 2/1976 | Nelson | 340/239 |
| 4,117,717 A | * 10/1978 | Isley | 73/38 |
| 4,198,853 A | * 4/1980 | Graham et al. | 73/38 |
| 4,366,717 A | * 1/1983 | Foord et al. | 73/744 |
| 4,389,879 A | * 6/1983 | Bach et al. | 73/61 R |
| 4,492,079 A | * 1/1985 | Takagi et al. | 60/274 |
| 4,583,396 A | * 4/1986 | Hunt et al. | 73/61 R |
| 4,614,109 A | * 9/1986 | Hoffmann | 73/38 |
| 4,667,504 A | * 5/1987 | Hobson | 73/38 |
| 4,676,092 A | * 6/1987 | Tuttle | 73/38 |
| 4,685,066 A | * 8/1987 | Hafele et al. | 364/509 |
| 5,095,740 A | * 3/1992 | Hodgson et al. | 73/61 R |
| 5,185,084 A | * 2/1993 | Lapidus et al. | 210/741 |
| 6,175,227 B1 | * 1/2001 | Graham et al. | 324/71.4 |
| 6,202,475 B1 | * 3/2001 | Gelbie et al. | 73/38 |
| 6,306,291 B1 | * 10/2001 | Lueck | 210/90 |

FOREIGN PATENT DOCUMENTS

| | | |
|---|---|---|
| DE | 38 40 901 | 6/1989 |
| JP | 8-101158 | 4/1996 |
| JP | 10-38836 | 2/1998 |

OTHER PUBLICATIONS

K.J. Kim, et al., Journal of Membrane Science, vol. 134, pp. 199–208, "Chemical and Electrical Characterization of Virgin and Protein–Fouled Polycarbonate Track–Etched Membranes by FTIR and Streaming–Potential Measurements", 1997.

Marianne Nyström, et al., Journal of Membrane Science, vol. 87, pp. 245–256, "Characterization of Ultrafiltration Membranes by Simultaneous Streaming Potential and Flux Measurements", 1994.

* cited by examiner

*Primary Examiner*—Hezron Williams
*Assistant Examiner*—David J. Wiggins
(74) *Attorney, Agent, or Firm*—Oblon, Spivak, McClelland, Maier & Neustadt, P.C.

(57) ABSTRACT

A membrane filtration method and an apparatus for continuously monitoring the state of a membrane during the filtration, particularly for membrane fouling due to cake or gel layers of solutes developed on the surfaces of a filtered membrane, by estimating a membrane potential and a membrane solute rejection while making measurements of a set of physical properties of feed, variations of a streaming potential difference across pores of the membrane, variation in pressure differences between an upstream side and a downstream side of the membrane, and concentration differences between the feed and permeate filtered through the membrane.

8 Claims, 4 Drawing Sheets

MEMBRANE FILTRATION METHOD AND APPARATUS FOR SIMULTANEOUSLY AND CONTINUOUSLY MONITORING TIME-BASED MEMBRANE FOULING

BACKGROUND OF THE INVENTION

1. Field of the Invention

The invention relates to a membrane filtration method and an apparatus for continuously monitoring the state of a membrane during the filtration. In particular, the present invention relates to a method and an apparatus for continuously monitoring for membrane fouling due to cake or gel layers of solutes developed on the surfaces of a filtered membrane.

2. Description of the Related Art

Membrane potential is based on the principles of electrostatics and electrokinetics. Membrane potential can provide useful information on physicochemical characteristics without disturbing the membrane filtration under the actual operating states or conditions. Solute rejection is an important factor indicating the filtration performance of a membrane, which can be determined by comparing the concentrations of a feed and a permeate.

Both the methods and the apparatus relating to the determination of membrane potential and membrane fouling are known in the art. According to K. J. Kim et al., Journal of Membrane Science, 134;199–208 (1997), the zeta potentials of virgin and fouled membranes were measured and a comparison based on the spectroscopic analysis was performed to investigate the changes of membrane potentials due to the membrane fouling. This article established that membrane potentials were altered before and after filtration through the intermittent measurements of membrane potentials of the fouled membranes at certain intervals. However, this paper has a disadvantage in that it cannot continuously confirm the behavior of the change of membrane potentials that are directly represented in the progress of membrane filtration under variable conditions. Consequently, in order to observe changes over the filtration time in membrane potentials, several identical membranes should be prepared and membrane potentials should be measured at specific intervals during the membrane filtration process. As a result, it is difficult to apply the results from Kim et al. to the real successive operating processes. In addition, a large number of membranes are actually required.

Journal of Membrane Science, 87:245–256, Elsevier (1994), discloses an apparatus which is capable of measuring simultaneously both membrane potentials and permeate fluxes. Flux measurements can be made simultaneously with the measurements of membrane potential. However, this apparatus is limited in that the correlation between solute rejections, membrane potentials, and permeate fluxes, cannot be identified. In particular, it is not possible to simultaneously monitor the solute rejections and the membrane potentials and, thus, impossible to identify the correlation between the solute rejections and the membrane potentials.

German Patent No. 3840901 discloses a membrane cell wherein horizontal channel flows are made on the surfaces of membranes in order to measure their zeta potentials. Such membrane cells do not permit for the membrane filtration and measurement of the zeta potentials to be conducted simultaneously. Also, as previously noted, the known membrane cells are not capable of monitoring the changes in characterization of the membrane over the passage of time.

Japanese Patent No. 8-101158 discloses a method for measuring streaming potentials associated with porous materials. Japanese Patent No. 10-38836 describes an apparatus for measuring streaming potentials. Both references show that the measurement of membrane potential cannot be performed simultaneously and continuously with the membrane filtration under specific operating pressure because the vessel for receiving the permeate is closed.

SUMMARY OF THE INVENTION

In order to solve the above-mentioned problems in the art, it is an object of the present invention to provide both a method and an apparatus which are capable of conducting membrane filtration simultaneously with the continuous measuring of potentials that are caused by minute differences in pressures between the upper and the lower surfaces of a membrane while also monitoring solute rejections due to variations in the concentration of the solution.

It is a further object to provide both a method and an apparatus that are capable of monitoring the progress of membrane fouling by continuously measuring the permeate flux, the membrane potential, and the solute rejection.

In order to accomplish these objects, the present invention provides for a membrane filtration method and an apparatus that continuously monitors for membrane fouling and changes in the membrane performance by simultaneously measuring the zeta potential of the membrane, solute rejection determined from the changes in the concentration, and the permeate flux. Essentially, the measurement of membrane potential according to the present invention is carried out by measuring streaming potentials originating from the inside of membrane pores and using the electrodes situated at both sides of the membrane while macromolecules, biopolymers, and inorganic aqueous solutions are filtered through the membrane.

The apparatus according to the present invention comprises a feed tank for receiving feed, a membrane module having an upper membrane cell and a lower membrane cell, a membrane situated between the upper and lower membrane cells, means for measuring properties of the feed, means for supplying the feed from the feed tank to the upper membrane cell of the membrane module, means for measuring a difference in the pressures between an upstream side and a downstream side of the membrane, means for measuring a streaming potential which builds inside of membrane pores, means for measuring concentration of the permeate which permeates through the membrane, and means for determining membrane fouling by estimating membrane potential using the physical properties of the feed, variations in the pressure difference between the upstream and downstream sides of the membrane and variations of the streaming potential difference, and estimating solute rejection of the membrane using the concentration difference between the feed and the permeate.

The apparatus further comprises means for measuring an amount of the permeate which is discharged from the lower membrane cell to obtain a permeate flux of the membrane.

The method for continuously monitoring the progress of membrane fouling over the filtration time using the apparatus of the present invention, comprises the steps of measuring properties of the feed that is fed from the feed tank to the upper membrane cell, measuring a difference in the pressures between the upstream side and the downstream side adjacent to the membrane, measuring a streaming potential developed inside of membrane pores, and obtaining a membrane potential using variation of the measured streaming potential, the properties of the feed and variation of the difference in the pressures between the upstream and the downstream sides of the membrane, measuring a concentration of the permeate which is passed through the membrane, and obtaining solute rejection of the membrane using measured concentration of the permeate and the concentration of the feed, and determining whether there is membrane fouling by simultaneously and continuously monitoring the estimated solute rejection and membrane potential.

The method further comprises the step of obtaining a permeate flux by measuring an amount of increase in the permeate per unit time. The present invention is described in more detail with reference to the accompanying drawings.

DETAILED DESCRIPTION OF THE INVENTION

Figure 1:
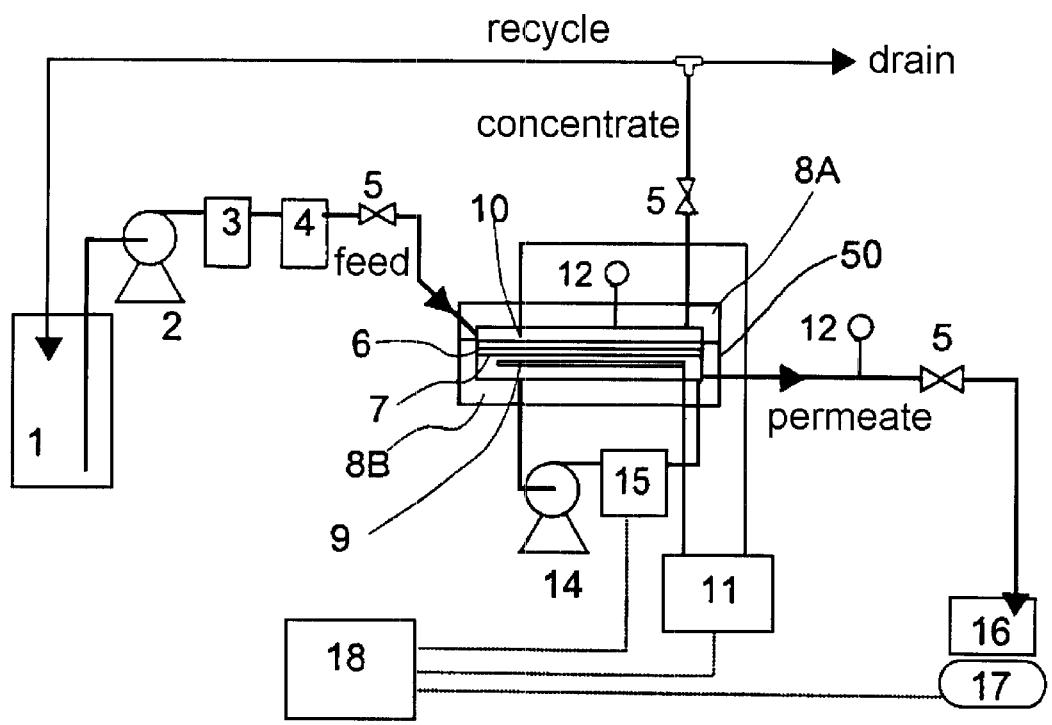
FIG. 1 is a schematic arrangement for the membrane filtration apparatus in accordance with the present invention.

FIG. 1 shows the schematics for the membrane filtration apparatus in accordance with the present invention. The membrane filtration apparatus according to the present invention basically comprises a thermostated feed tank (1) for receiving a feed to be filtered through a flat-sheet membrane (6), a membrane module (50) having the flat-sheet membrane (6), means for measuring values of properties of the feed, means for measuring a difference in the pressures between an upstream side and a downstream side of the membrane, means for measuring a streaming potential of the membrane, means for measuring a concentration of the permeate which is passed through the membrane, means for determining the progress of the membrane fouling and the replacement timing of the fouled membrane by collecting the data obtained from the measuring means and estimating a membrane potential and a solute rejection of the flat-sheet membrane (6).

Figure 2:
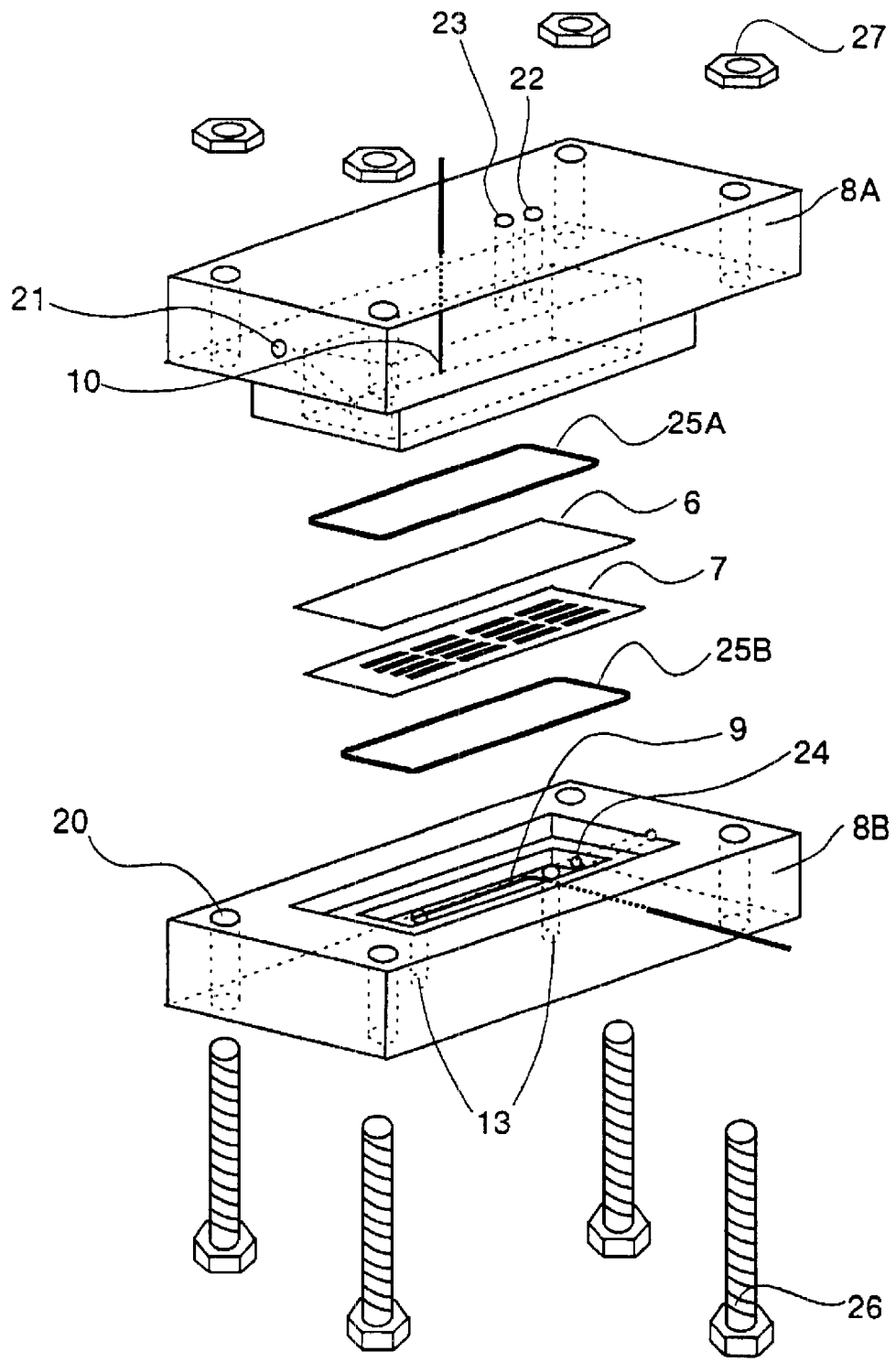
FIG. 2 is an exploded, perspective view showing the different components which make up the membrane module in accordance with the present invention.

Referring to FIG. 2, the membrane module (50) includes an upper membrane cell (8A), a lower membrane cell (8B), a flat-sheet membrane (6) situated between the upper membrane cell and the lower membrane cell, and a membrane supporter (7) for supporting the membrane at a lower portion thereof. The upper membrane cell (8A) is equipped with a feed inlet (21) and a concentrate outlet (22). The feed inlet (21) is connected to the thermostated feed tank (1). The concentrate outlet (22) returns or discharges the concentrate, which is not filtered through the membrane, to the thermostated feed tank (1). The lower membrane cell (8B) is equipped with a permeate flow path (13) and a permeate outlet (24). The permeate flow path (13) is formed such that a portion of the permeate may be bypassed for measuring a concentration of the permeate with only a fraction of the permeate. As shown in FIG. 1, the permeate outlet (24) is formed such that the portion of the permeate for measuring the concentration and the remainder of the permeate may be discharged together to a permeate receiving container (16). FIG. 2 shows that between the upper membrane cell (8A) and the lower membrane cell (8B) the following are positioned in order, an upper sealing ring (25A), the membrane (6), the membrane supporter (7) and a lower sealing ring (25B). Thereafter, both the upper membrane cell and the lower membrane cell are brought together and assembled with bolts (26) and nuts (27) through the membrane cell connecting apertures (20).

Referring back to FIG. 1, the feed contained in the thermostated feed tank (1) enters the upper membrane cell (8A) through the feed inlet (21) by a solvent delivering pump (2). Both the flux and the pressure of the feed supplied from the thermostated feed tank (1) to the upper membrane cell (8A) are controlled by a minute flow control valve (5). Electrical conductivity and pH of the feed are measured with a conductance meter (3) and a pH-meter (4). A pressure sensor (12) is connected through a pressure sensor connecting aperture (23) into a space that is defined by the upper membrane cell (8A) and the membrane (6), and another pressure sensor (12) is situated in a downstream side of a permeate outlet (24). Differences in the pressure between the upstream side and the downstream side of the membrane (6) are measured with the pressure sensors (12). The feed entered through the feed inlet (21) has a tangential flow and is divided into a concentrate and a permeate. The concentrate is discharged to the concentrate outlet (22) and the permeate is discharged to the permeate outlet (24). In order to measure streaming potentials (V) that are developed inside of membrane pores as a result of the permeate flow through the channel of membrane pores, Ag/AgCl upper and lower electrodes (9, 10) are situated in a space between the upper membrane cell (8A) and the membrane (6) and in another space between the lower membrane cell (8B) and membrane (6), respectively. In particular, it is desirable that the lower electrode (10) is spaced no greater than 0.02 cm from a membrane support (7) for supporting the membrane (6) so that it has a surface area of about 5% of an effective area of the membrane. Thus, when differences in the pressure are controlled within the range of about 20% of the operating pressure at any time that is intended to measure membrane potentials, undisturbed membrane filtration can be carried out continuously, and also minute variations for potentials can be precisely detected with a digital multimeter (11).

As means for measuring concentrations of a permeate which pass through the membrane (6), detectors such as a UV detector, a refractive index detector, a fluorescent detector, etc., based on optical principles, are preferably used. Concentrations of a permeate are measured in such a way that a minimum amount of permeate needed for optical detection is bypassed with the permeate delivering pump (14) through the permeate flow path (13) which is formed in the lower membrane cell (8B). Subsequently, a minimum amount of the permeate is conveyed to a photo cell of a UV detector (15) which is arranged to communicate with the permeate flow path (13). Solute rejections are then measured without impeding the membrane filtration and membrane potentials. In addition, the total permeate passed through the membrane is delivered to the permeate receiving container (16) through the permeate outlet (24) which is formed in the lower membrane cell (8B). The permeate delivered to the container (16) per unit time is then weighed, for example, on an electronic balance (17).

The aforementioned measurement values such as electric conductivity (λ) of the solution, pH, streaming potential (V) of the membrane, difference in the pressure (ΔP) between both ends of the membrane, and variation of the amount of permeate per unit time are sent to a computer (18). Along with dielectric constant (∈) and viscosity (η) of the feed used, the zeta potentials (ζ) as membrane potentials are estimated using the Helmholtz-Smoluchowski equation below.

$$\frac{\Delta V}{\Delta P} = \frac{\epsilon \zeta}{\lambda \eta} \qquad \text{(Equation 1)}$$

At the same time, data for the concentrations of the permeate ($C_{permeate}$) and the concentrations of the feed ($C_{feed}$), which are measured with the concentration measuring apparatus, are sent to a data acquisition software installed in a computer (18). Solute rejections ($R_j$,) are then obtained according to the following equation.

$$R_j(\%) = \frac{C_{feed} - C_{permeate}}{C_{feed}} \times 100 \qquad \text{(Equation 2)}$$

In addition, permeate fluxes are obtained from the computer (18) by measuring the weight of the permeate that is collected to the permeate receiving container (16) per unit time using the electronic balance (17).

The following examples demonstrate practical results obtained from experiments and analyses using the method and the apparatus according to the present invention.

EXAMPLE 1

Figure 3:
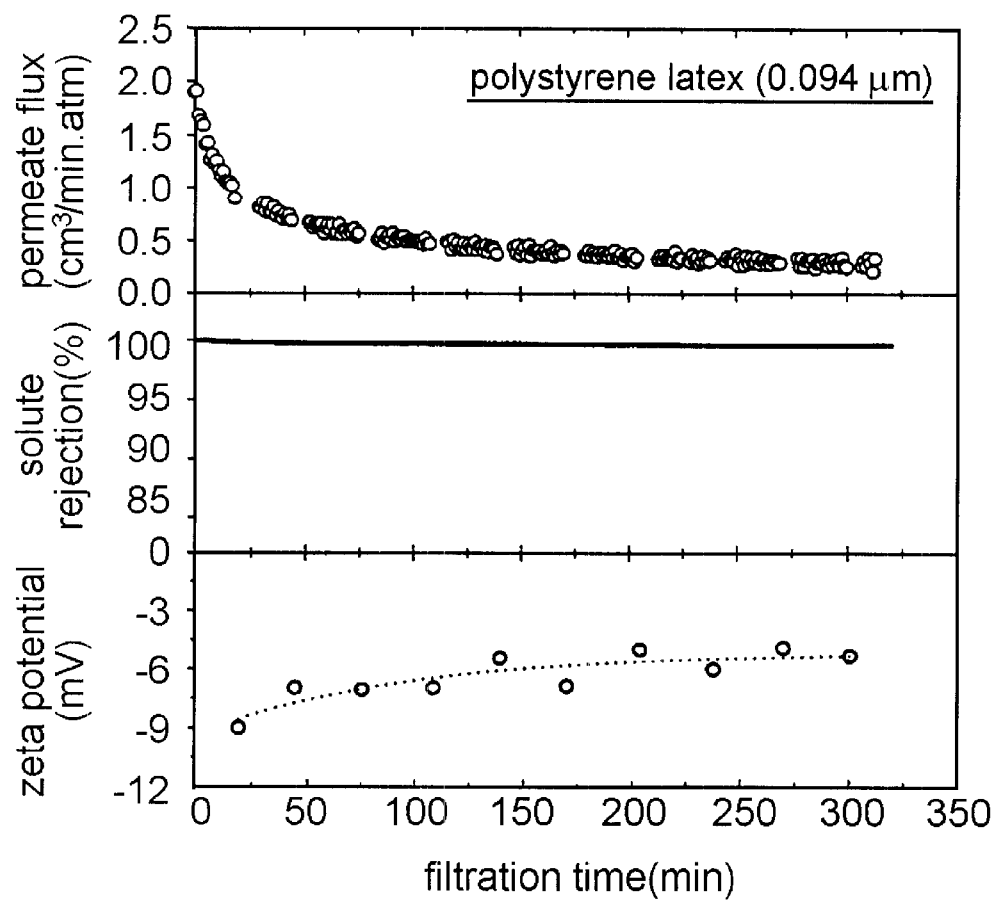
FIG. 3 is a graph which plots permeate flux, solute rejection, and membrane potential measured over the filtration time while a suspension of 0.02 weight % polystyrene latex composed of spherical colloid particles is filtered at a specific operating pressure using the membrane filtration apparatus of the present invention.

A membrane cell equipped with polycarbonate track-etched UF (ultrafiltration) membranes (Poretics, CA) having symmetric cylindrical pores was used. A suspension of polystyrene latex (Sigma Chemical Co.) of 0.02 weight percent comprising spherical particles having diameter of 0.094 gm was prepared by dispersing in 1.0 mM KCl electrolyte solution (pH 6.4). The suspension was allowed to flow into the upper membrane cell (8A) using the solvent delivering pump (2). Filtration through the membrane was carried out under a transmembrane pressure difference of 100 kPa by controlling the minute flow control valve (5). Membrane potentials were measured from the streaming potentials that were produced in the pores of the membrane, solute rejections measured with the UV detector using a portion of the permeate, and permeate fluxes were measured from the amount of the total permeate. As shown in FIG. 3, as the filtration of the particles is progressed, the cake layers of latex particles are formed on the surfaces of the membrane. As a result, the permeate flux gradually decreased and then remained a constant. With regard to the measurement of the solute rejection of the membrane, since the size of the latex particles was greater than that of the membrane pores, a complete rejection of the solute particles was maintained. From the foregoing, it can be understood that the membrane reveals a decrease in the permeate flux while the membrane shows a constant in the solute rejection with the passage of the filtration time. Further, as shown in FIG. 3, membrane potential is illustrated as being continuously changed due to the formation of cake layers on the surface of the membrane during the filtration of the particles. This illustrates that membrane potential converges to a constant value when the permeate flux is no longer decreased.

EXAMPLE 2

Figure 4:
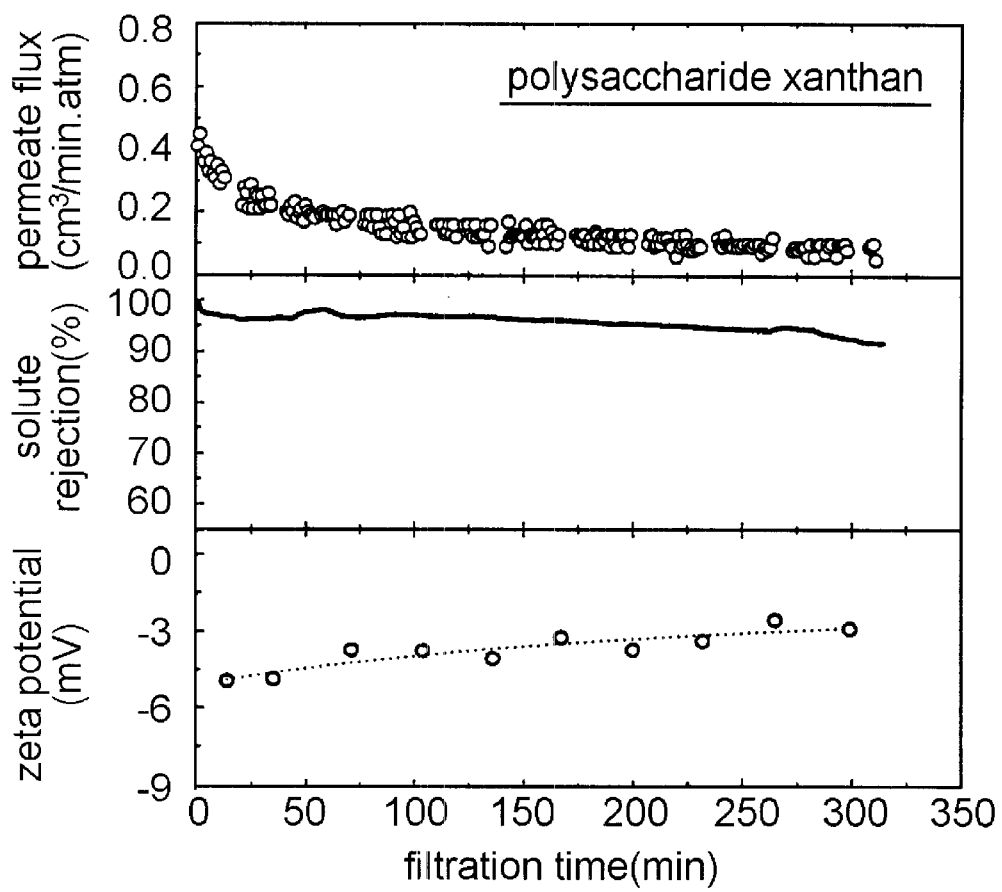
FIG. 4 is a graph which plots permeate flux, solute rejection, and membrane potential measured over the filtration time while a solution containing 0.01 weight % xanthan gum as an example of a biopolymeric polysaccharide is filtered at a specific operating pressure using the membrane filtration apparatus of the present invention.

A membrane cell was equipped with polycarbonate track-etched UF membranes (Poretics, CA) having symmetric cylindrical-shaped pores. A suspension containing biopolymer xanthan gum of 0.01 weight percent was prepared by dispersing it in 1.0 mM KCl electrolyte solution (pH 5.7). The xanthan gum used was a polymeric polyelectrolyte compound with average molecular weight of $1.1 \times 10^6$. The suspension was allowed to flow into the upper membrane cell (8A) using the solvent delivering pump (2). Filtration was carried out under a transmembrane pressure difference of 100 kPa by controlling the minute flow control valve (5). As shown in FIG. 4, as the filtration of the suspension is progressed, gel layers of xanthan gum are formed on the surface of the membrane. As a result, the permeate flux gradually decreased and then settled at a constant value. In FIG. 4, it can be seen that the membrane tends to reveal a gradual decrease in the solute rejection during the course of filtration. With regard to the gradual decrease in the solute rejection, it is believed that the membrane reveals a complete rejection behavior at the beginning of the filtration, but portions of xanthan gum are passed through the pores due to the semi-flexible nature of xanthan gum when the gel layers are deposited onto the pores of the membrane and then the pressure is exerted on them. Moreover, variations of the membrane potential resulting from the formation of gel layers on the surface of the membrane are illustrated throughout the course of filtration. In this case, the membrane tends to reach a constant zeta potential over the time.

As can be seen from FIGS. 1 and 2 and Examples 1 and 2, both the method and the apparatus of the present invention allow continuous measurements of permeate fluxes, solute rejections, and membrane potentials over the filtration time simultaneously with the filtration of solute particles through the membrane pore. According to the method and the apparatus of the present invention, permeate fluxes, solute rejections and membrane potentials can be simultaneously and continuously monitored without impeding the progress of filtration through the membrane pore. Thus, the progress of membrane fouling can also be continuously monitored.

According to the present invention, the state of membrane fouling can be continuously observed with only a membrane equipped initially, and the efficient processes of membrane filtration are provided. In particular, useful information can be obtained for determining the time when the membrane fouling begins, the duration of the development of membrane fouling, and the time for replacement of the membrane.

While the invention has been presented with exemplary embodiments as described above, they are in no way intended to limit the scope of the present invention. One skilled in the art will appreciate modifications and adaptations after having the benefit of this disclosure. All such modifications and adaptations are intended to be within the spirit and scope of the presently claimed invention which is presented below.

What is claimed is:

1. A membrane filtration apparatus for continuously monitoring progress of a membrane fouling over a filtration time, while simultaneously performing a filtration of solutes from a feed, comprising:

a feed tank for receiving a supply of the feed;

a module having an upper membrane cell, a lower membrane cell and a membrane having pores and situated between the upper and lower membrane cells, and the module for permitting passage of a filtered permeate between the upper and lower membrane cells, means for measuring a set of physical properties of the feed;

means for supplying the feed from the feed tank to the upper membrane cell of the module;

means for measuring any variations or differences in the pressure between an upstream side and a downstream side of the membrane;

means for measuring differences of a streaming potential across the membrane pores;

means for measuring concentration of the permeate filtered through the membrane; and means for determining the membrane fouling by estimating a membrane potential using the physical properties of the feed, variations in the pressure difference between the upstream and downstream sides of the membrane and variations of the streaming potential difference, and by estimating a degree of solute rejection of the membrane using a concentration difference between the feed and the permeate.

2. The apparatus according to claim 1, further comprising means for measuring amounts of permeate discharged from the lower membrane cell to obtain a permeate flux of the membrane.

3. The apparatus according to claim 1 or 2, wherein the means for measuring the concentration of the permeate includes a permeate flow path for bypassing a portion of the permeate without impeding the filtration in the membrane, and a detector for detecting the concentration of the permeate bypassed through the permeate flow path, having both an inlet and an outlet serially connected through the interior of the lower membrane cell.

4. The apparatus according to claim 1 or 2, wherein the means for measuring the differences of the streaming potential includes an upper electrode and a lower electrode respectively positioned in the upper and the lower membrane cells.

5. A method of continuously monitoring progress of a membrane fouling over a filtration time, while simultaneously performing a filtration of solutes from a feed, using the apparatus according to claim 1, comprising the steps of:

measuring a set of properties of the feed that is fed from the feed tank to the upper membrane cell;

measuring differences in the pressure between the upstream side and the downstream side of the membrane;

measuring differences of the streaming potential across the membrane pores and obtaining a membrane potential using variation of the measured streaming potential difference, the properties of the feed and the differences in the pressure between the upstream and the downstream sides of the membrane;

measuring concentration of the permeate which is passed through the membrane pore and obtaining estimated solute rejection of the membrane using the measured concentration of the permeate and concentration of the feed; and detecting membrane fouling while simultaneously and continuously monitoring the estimated solute rejection and membrane potential.

6. A method of continuously monitoring progress of a membrane fouling over a filtration time, while simultaneously performing a filtration of solutes from a feed, using the apparatus according to claim 2, comprising the steps of:

measuring a set of properties of the feed that is fed from the feed tank to the upper membrane cell;

measuring differences in the pressure between the upstream side and the downstream side of the membrane;

measuring differences of the streaming potential across the membrane pores and obtaining a membrane potential using variation of the measured streaming potential difference, the properties of the feed and the differences in the pressure between the upstream and the downstream sides of the membrane;

measuring concentration of the permeate which is passed through the membrane pore and obtaining estimated solute rejection of the membrane using the measured concentration of the permeate and concentration of the feed;

detecting membrane fouling while simultaneously and continuously monitoring the estimated solute rejection and membrane potential; and obtaining a permeate flux by measuring amounts of increase of permeate per unit time.

7. The method according to claim 5, wherein the step of measuring the concentration of the permeate is carried out using a minimum amount of the permeate passed through a permeate flow path formed in the lower membrane cell such that a portion of the permeate is bypassed therethrough without impeding the filtration in the membrane.

8. The method according to claim 6, wherein the step of measuring the concentration of the permeate is carried out using a minimum amount of the permeate passed through a permeate flow path formed in the lower membrane cell such that a portion of the permeate is bypassed therethrough without impeding the filtration in the membrane.

* * * * *

UNITED STATES PATENT AND TRADEMARK OFFICE
CERTIFICATE OF CORRECTION

PATENT NO.     : 6,463,790 B1
DATED          : October 15, 2002
INVENTOR(S)    : Chun et al.

It is certified that error appears in the above-identified patent and that said Letters Patent is hereby corrected as shown below:

<u>Title page,</u>
Item [30], Foreign Application Priority Data, should read:
-- [30]   Foreign Application Priority Data
May 24, 2000 (KR) ………………………….. 2000-27910 --

Signed and Sealed this

Eighteenth Day of February, 2003

JAMES E. ROGAN
*Director of the United States Patent and Trademark Office*